(12) United States Patent
Kraus

(10) Patent No.: US 6,194,214 B1
(45) Date of Patent: Feb. 27, 2001

(54) USE OF ANNEXINS AS A LUPUS ANTICOAGULANT CONTROL OR STANDARD IN CLOTTING TESTS

(75) Inventor: Michael Kraus, Marburg (DE)

(73) Assignee: Dade Behring Marburg GmbH, Marburg (DE)

( * ) Notice: Subject to any disclaimer, the term of this patent is extended or adjusted under 35 U.S.C. 154(b) by 0 days.

(21) Appl. No.: 09/131,773

(22) Filed: Aug. 10, 1998

(30) Foreign Application Priority Data

Aug. 11, 1997 (DE) .............................. 197 34 648

(51) Int. Cl.$^7$ .................................. G01N 33/86
(52) U.S. Cl. .................. 436/16; 435/13; 436/8; 436/69
(58) Field of Search .................. 436/8, 16, 15, 436/69, 86; 435/13

(56) References Cited

U.S. PATENT DOCUMENTS

| | | | | |
|---|---|---|---|---|
| 4,507,229 | * | 3/1985 | Bohn | 260/112 |
| 4,877,741 | * | 10/1989 | Babcock | 436/8 |
| 5,097,019 | * | 3/1992 | Lobermann | 530/392 |
| 5,726,028 | * | 3/1998 | Kraus | 435/13 |
| 5,753,510 | * | 5/1998 | Kraus | 436/16 |
| 5,763,403 | * | 6/1998 | Lian | 514/12 |
| 5,922,587 | * | 7/1999 | Triplett | 435/212 |

FOREIGN PATENT DOCUMENTS

| | | |
|---|---|---|
| 0123 307 | 4/1984 | (EP) . |
| 0271 885 | 12/1987 | (EP) . |

OTHER PUBLICATIONS

Rauch et al, Thrombosis and Haemostasis, 1989;62(3) 892–896.*
Messmore et al, Seminars in Thrombosis and Hemostasis, 1994;20(1) 79–88.*
Romisch et al, Thrombosis Research, 1990; 60:355–366.*
McGlasson et al, Coagulation and Transfusion Medicine, 1993; 100:576–578.*
Rand et al, Blood; 1998; 92(5) 1652–1660.*
Amout, J. et al., "Optimization of the Dilute Prothrombin Time for the Detection of the Lupus Anticoagulant by Use of a Recombinant Tissue Thromboplastin," *British Journal of Haematology*, vol. 87, 1994, pp. 94–99.
Brandt, John T., "Assays for Phospholipid–Dependent Formation of Thrombin and Xa: A Potential Method for Quantifying Lupus Anticoagulant Activity," *Thrombosis and Haemostasis*, vol. 66, 1991, pp. 453–458.

Brandt, John T. et al., "Criteria for the Diagnosis of Lupus Anticoagulants: An Update," *Thrombosis and Haemostasis*, 1995, pp. 1185–1190.

Brauer, P., et al., The Tissue Thromboplastin Inhibition Test with Thromborel S: Test Design and Standardisation, *J. Clin. Chem. Clin. Biochem.*vol. 28, 1990, p. 701.

McGlasson, David L. et al., "ARACHnase—An Evaluation of a Positive Control for Platelet Neutralization Procedure Testing With Seven Commercial Activated Partial Thromboplastin Time Reagents," *Coagulation and Transfusion Medicine*, vol. 100, 1993, pp. 576–578.

Messmore, M.D., Harry et al., "Lupus Anticoagulant Assays," *Seminars in Thrombosis and Hemostasis*, vol. 20, 1994, pp. 79–88.

Rauch, Joyce et al., "Distinguishing Plasma Lupus Anticoagulants from Anti–Factor Antibodies Using Hexagonal (II) Phase Phospholipids," *Thrombosis and Haemostasis*, vol. 62, 1989, pp. 892–896.

Robert, Annie, "Two Different Incubation Times for the Activated Partial Thromboplastin Time (APTT): a New Criterion for Diagnosis of Lupus Anticoagulant," *Thrombosis and Haemostasis*, vol. 71, 1994, pp. 220–224.

Römisch, Jürgen et al., "Purification and Characterization of Six Annexins from Human Placenta," *Biol. Chem. Hoppe–Seyler*, vol. 371, 1990, pp. 383–388.

Römisch, Jürgen et al., "Anticoagulant Properties of Placenta Protein 4 (Annexin V)," *Thrombosis Research*, vol. 60, 1990, pp. 355–366.

Triplett, M.D., Douglas A. et al., "Lupus Anticoagulants: Misnomer, Paradox, Riddle, Epiphenomenon," *Hematologic Pathology*, vol. 2, 1988, pp. 121–143.

* cited by examiner

*Primary Examiner*—Jan Ludlow
(74) *Attorney, Agent, or Firm*—Finnegan, Henderson, Farabow, Garrett and Dunner, L.L.P.

(57) ABSTRACT

The invention relates to a process for the production of plasmas with added annexins for use as a control or standard in all functional clotting tests which are used for the detection of a lupus anticoagulant.

22 Claims, No Drawings

USE OF ANNEXINS AS A LUPUS ANTICOAGULANT CONTROL OR STANDARD IN CLOTTING TESTS

The invention relates to a process for the production of plasmas for use as a control or standard in all functional clotting tests which are used for the detection of a lupus anticoagulant.

Lupus anticoagulants are immunoglobulins and belong to the acquired autoantibodies type. They are directed against phospholipids or phospholipid/protein complexes and prolong the clotting time in customary diagnostic clotting tests (see Triplett D., et al. Hematologic Pathology 1988; 2: 121–143). These immunoglobulins are to be differentiated from other autoantibodies likewise against lipids, in particular cardiolipins. Both groups are clinically assigned to the antiphospholipid syndrome (APS) which manifests itself in thromboses and an increase in birth complications (miscarriages). The pathological mechanism of the lupus anticoagulants is still unclarified for several reasons. Firstly, the specificity of the occurring antibodies and thus the mechanism of action is individually different from patient to patient. Secondly, the subclasses of the immunoglobulins (IgM, IgG, IgA) and the antibody titers vary. Thirdly, there is a paradox between the determination of the lupus anticoagulant and clinical manifestation: a prolongation of the clotting time in in vitro tests, as is caused by lupus anticoagulant, points to an increased proneness to bleeding, in vivo, however, it is manifested in an increased proneness to thromboses.

The diagnosis of a lupus anticoagulant is therefore restricted to a phenomenological, description of the behavior of a plasma sample in various clotting tests according to the recommendations of international committees (Brandt, J. T. et al., Thrombosis Haemostasis 1995; 74: 1185–1190). These tests are the activated partial thromboplastin time (APTT), the kaolin clotting time (KCT) the dilute thromboplastin time (dPT) and the Russell's viper venom time (RVVT). A prolongation of the clotting time in these tests, however, is also obtained by a factor deficiency, which is why in the so-called plasma exchange test the pathological sample is mixed with normal plasma and as a rule determined in the APTT. A factor deficiency, as a rule, is already compensated for in a substitution of 50% by mixing with the normal plasma, while in the presence of a lupus anticoagulant pathological results are still obtained. Furthermore, the phospholipid dependence is to be checked, which is carried out using the same reagents, but with different concentrations of phospholipids. Furthermore to be differentiated are autoantibodies against individual clotting factors, which are likewise not compensated for by 1+1 mixing with a normal plasma. As a rule, these factor antibodies, however, only act in one of the two pathways of the clotting system (in particular so-called Factor VIII inhibitors) and are recognized by the comparison of the various pathways, i.e. by the comparison of the abovementioned tests (APTT for the intrinsic, PT for the extrinsic pathway).

The sensitivity of the reagents of the abovementioned tests to lupus anticoagulant is very different (Messmore, H., et al., Thrombosis and Hemostasis. 1994, 20: 79–94). Furthermore, lupus anticoagulants do not produce a pathological result in all tests, which is why the use of at least two functional tests is recommended (for example the APTT and the RVVT; see Brandt, J. T. et al.,Thrombosis Haemostasis 1995; 74: 1185–1190). For comparison or exchange of data, e.g. in clinical studies, reference to a standard would therefore be useful, as well as regular checking of the test results, for example for monitoring a therapy. The use of individual plasma donors is unsuitable for the preparation of such a standard or a control for commercial use, however, because of the heterogeneity of the specificity, the low reproducibility and the poor stability of lupus anticoagulants. At present therefore, there is neither a clear determination of a lupus anticoagulant nor a reference to the quantification of a lupus anticoagulant.

The invention was therefore based on. the object of finding a process with which, in a sample, e.g. plasma, a lupus anticoagulant can be reproducibly and quantifiably simulated in such a way that this modified plasma produces pathological results comparable with the presence of a natural lupus anticoagulant in all customary functional clotting tests and is thus suitable for quantification of the action (standard) and as a control.

An essential characteristic of the lupus anticoagulant is the dependence of the clotting-prolonging property on the availability of the phospholipids. One possibility of simulating this behavior was described by Babcock and McGlasson (U.S. Pat. No. 4,877,741). They use an extract from a spider (Loxosceles reclusa) which contains an enzyme having a sphingomyelinase D activity. They were able to show (McGlasson, D. L. et al., Am. J. Clin. Pathol 1993; 100: 576–578) that this extract in the APTT leads with various reagents to a prolongation of the clotting time and can be neutralized by addition of phospholipids. This prolongation, however, is only weakly pronounced. Thus the prolongation achieved was at most 63% of the upper standard range (APTT reagent from Pacific Hemostasis; Table 2; (McGlasson, D. L. et al., Am. J. Clin. Pathol 1993; 100: 576–578). This is too low in order to produce typical prolongations of more than 100%, as occur with high lupus anticoagulant and therefore not adequate for standardization using.a wide measuring range.

It has also been described that annexins under certain circumstances can lead to a prolongation of the APTT.

This family of intracellular proteins at present includes at least eight characterized proteins which are designated according to. the new nomenclature as annexin I to VIII (R ömisch, J. et al., Biol, Chem. Hoppe Seyler 1990; 5: 383–388). These proteins have an inflammation-modulating action in that they are released from cells on inflammation and bind to membrane surfaces and thereby inhibit the binding of phospholipase A2, an important step for the formation of arachidonic acid derivatives having an inflammatory activity. By means of this calcium-dependent binding to phospholipid surfaces, the clotting processes taking place on these surfaces are also disturbed, which is why these proteins are also designated as "vascular anticoagulant". Typically, the presence of annexins leads to a prolongation of the APTT in a concentration-dependent manner (R ömisch et al. Thrombosis Research 1990; 60: 355–366).

Until now, however, it was unknown whether annexins could fulfill all criteria comparably to a natural lupus anticoagulant. The following criteria are used for the functional diagnosis of a lupus anticoagulant (Brandt, J. T. et al., Thrombosis Haemostasis 1995; 74: 1185–1190):

1. Prolongation of the clotting time beyond the normal range in at least two tests, in particular the APTT and the RVVT.
2. Proof that this prolongation is phospholipid-dependent and can be neutralized either by addition of phospholipids or by use of the same reagents as in 1. only with higher phospholipid concentrations.
3. Differentiation of a possible factor deficiency by plasma exchange experiments, in which case, in a 3+1, 1+1 and 1+3 mixture with a normal plasma in a clotting test, preferably the APTT, this prolongation is characteristically only neutralized by a high dilution (1+3), while in the case of a factor deficiency this is already clear earlier.

4. Differentiation of an acquired inhibitor (auto antibody against a clotting factor), in particular against Factor IX or Factor VIII (acquired hemophilia A or B) wherein this only acts in one of the two clotting pathways (intrinsic or extrinsic pathway), while a lupus anticoagulant non-specifically affects all phospholipid-dependent stages in clotting tests.

Surprisingly, it was now possible to show that by the suitable use of annexins a lupus anticoagulant standard or control preparation can be prepared which fulfills all the criteria described above.

Example 1 shows the prolongation of the customary diagnostic clotting tests, the APTT, the PT and the RVVT on addition of an annexin (annexin V) to a plasma pool from normal blood donors (standard human plasma). With an addition of 125 $\mu$g of annexin V, prolongations of the clotting times of 470%, 31% and 200% above the upper normal range of the respective reagents were attained. This shows that, compared with the present state of the art (McGlasson, D. L. et al., Am. J. Clin. Pathol 1993; 100: 576–578) markedly higher prolongations of the clotting times and thus the possibility of the preparation of a standard and thus of reaching a further calibration range was improved. In the PT, this prolongation is not as strongly pronounced. In contrast to the APTT and RVVT, the PT is not recommended as a diagnostic test for lupus anticoagulants.

Example 1 thus shows the fulfillment of criterion 1 of lupus diagnosis, i.e. a pathological result in at least 2 functional clotting tests, in particular the APTT and the RVVT. The two natural lupus anticoagulant-positive plasmas behave comparably.

In Example 1, a plasma with factor deficiency, or a plasma with an acquired inhibitor, for example, were also tested. The deficiency of Factor VIII or of the acquired inhibitor against Factor VII only leads to pathological results in the APTT and not also, like the annexin-containing plasma or the natural lupus anticoagulant-positive plasmas, in the PT or the RVWT. Criterion 4 of lupus anticoagulant diagnosis is thus also fulfilled.

Example 2 shows the results of the testing of phospholipid dependence in the APTT, the PT and the RVVT. Reagents having a phospholipid content which was modified compared with the reagents used in Example 1 were used. The ratio of the clotting time at low phospholipid concentration compared with that at high phospholipid concentration is increased in plasmas in which a lupus anticoagulant is suspected compared with normal plasmas. This behavior is only recorded in the required APTT and RVVT in the case of the natural and the simulated lupus anticoagulant-containing plasma. The PT is also pathological in this case. Thus criterion 2 of the lupus diagnosis is fulfilled. The normal plasma pool, as well as the factor-deficient plasma, appear to be nonpathological. Only the plasma with an acquired factor inhibitor remains prolonged in the process based on the APTT.

Example 3 shows the results of testing for factor deficiency by means of plasma exchange experiments in the APTT. In the case of a mixture of 1+3 with the normal plasma pool, all pathological plasmas, as well as the simulated lupus anticoagulant-positive plasma, are prolonged. In the case of a 1+1 dilution, the deficiency in the factor-deficient plasma is already adequately compensated. The clotting time is in the normal range. Annexin-containing plasmas, the natural, lupus anti-coagulant-positive plasmas, as well as the factor inhibitor-containing plasma are still pathological in the test. This shows, on the one hand, the fulfillment of the 3rd and last criterion for the diagnosis of a lupus anticoagulant and thus the possibility of employing annexins for the simulation of a lupus anticoagulant for use as calibrators or controls in functional clotting tests.

Example 3 furthermore shows that for the fulfillment of the 3rd criterion, the plasma exchange experiment, the anticoagulatory active concentration of the annexin in a control must be adjusted such that in a 1+3 dilution with a normal plasma pool in an APTT a pathological result is still obtained. In the undiluted state, this corresponds in these examples to an addition of at least 7 mg/l of annexin V. Even in the case of this minimum amount, in the undiluted plasma a prolongation of the clotting time beyond the upper normal range of 87% is thus achieved (see Example 1, Table 1, APTT few PL). This requirement has not been possible by means of previously described processes (McGlasson, D. L. et al., Am. J. Clin. Pathol 1993; 100: 576–578) and thus it was not possible with plasmas prepared by this previous process to produce a lupus anticoagulant-like behavior in the plasma exchange experiment. The inventive process is thus clearly superior to the previous process.

Apart from the functional clotting tests shown in the examples, the control or calibrator plasmas according to the invention can also be used in other functional clotting tests known to the person skilled in the art (Messmore, H. et al., Thrombosis Haemostasis 1994; 71: 220–224.; Brandt, J. T., Thrombosis Haemostasis 1991; 66: 453–458; Arnout, J. et al., Brit. J. Haematol. 1994; 87: 94–99; Rauch, J. et al., Thrombosis Haemostasis 1989; 62: 892–896).

Apart from the annexin V used in the examples, other proteins from the annexins family can also be used individually or as mixtures of various annexins for the preparation of control and/or calibrator plasmas. Advantageously, in this case both annexing purified from known natural sources (EP 0 123 307) or prepared by recombinant means (for example EP 0 271 885) are used.

In a control plasma, the concentration of these annexins is preferably selected such that even at a dilution of this control plasma of 1+3 with a normal plasma pool an APTT above the normal range is still obtained. In the case of adjustment of the control to other clotting tests, it is possible for these threshold concentrations to differ from one another in a reagent- and test specific manner.

For calibrator plasmas, the concentrations of the annexins are ideally selected such that the clotting times obtained therewith are above the respective test and reagent used.

From the use of defined amounts of annexins for production of a prolongation of the clotting time, the possibility results of the calibration of antibody titers of lupus anticoagulant-positive plasmas, for example, in mg/l of annexin equivalent.

A The following examples illustrate the invention.

If not stated otherwise, reagents and plasmas from Behringwerke are used for the examples below.

EXAMPLE 1

Behavior of an annexin-containing plasma in diagnostic clotting tests in comparison with various normal and pathological plasmas.

A normal plasma pool (standard human plasma) was mixed with 4 to 500 mg/l of recombinant annexin V (prepared according to EP 0 271 885) and the clotting times in the APTT (reagent: Pathromtin SL or Pathromtin SL with a 10-fold higher phospholipid concentration than in pathromtin SL), the PT (reagent: Thromborel S) and the RVVT (regent: LA screen; manufacturer: Gradipore, Australia) on an automatic clotting apparatus (Amelung, Germany).

Table 1 shows the prolongation of the customary diagnostic clotting tests, the APTT, the PT and the RVVT on addition of an annexin (annexin V) to a normal plasma pool. With an addition of 125 μg of annexin V, the clotting times were prolonged by >400%, 31% and 200% above the upper normal range of the respective reagents (APTT: 38 sec or 49 sec; PT: 13 sec; RVVT: 45 sec; the instructions of the manufacturer).

TABLE 1

Effect of annexin V in a normal plasma pool (NPP) on the diagnostic clotting tests, APTT, PT and RVVT.

| Content of annexin V in NPP (in mg/l) | APTT [sec] many PL | APTT [sec] few PL | PT [sec] many PL | RVVT [sec] few PL |
|---|---|---|---|---|
| 0 | 38.0 | 45.5 | 13.0 | 38.8 |
| 3.8 | 37.6 | 59.1 | | |
| 7.3 | 38.8 | 91.6 | | |
| 15.5 | 40.1 | 149.3 | | |
| 31.3 | 345.0 | 186.3 | | |
| 62.5 | 81.7 | 211.6 | 15.0 | 122.6 |
| 125 | 215.9 | 262.5 | 17.0 | 135.1 |
| 250 | 233.5 | 270.0 | 21.2 | 139.4 |
| 500 | 320.6 | 316.0 | 34.5 | 152.8 |

Furthermore, using these diagnostic tests the clotting times of the following pathological plasmas were determined:

Factor VIII-deficient plasma (Prod. No. OTXW) for the simulation of a factor deficiency;

a citrate plasma of a patient with acquired Factor VIII inhibitor (George King, USA);

2 citrate plasmas of patients with proven lupus anticoagulant (Trina, Switzerland).

Table 2 shows the results of determination of the APTT, the PT and the RVVT in the various plasmas. The normal plasma pool is within the normal range in all 3 tests. The Factor VIII-deficient plasma, however, is pathological in the APTT, as well as the plasma with an acquired Factor VIII inhibitor. Both plasmas are only slightly pathological in the PT, but nonpathological in the RVVT. In contrast to this, the two natural lupus anticoagulant-positive plasmas are pathological in all tests, even if marked to a differingly high extent. This nonspecific prolongation of the clotting times in the diagnostic clotting tests is produced in an identical manner by the addition of annexin to a normal plasma pool (the results from Table 1 with an addition of 125 mg/l or 62.5 mg/l of annexin were assumed in Table 2).

TABLE 2

Behavior of a normal plasma pool (NPP), a plasma with factor deficiency (FVIII-MP) or inhibitor against Factor VIII (anti-FVIII-P), natural lupus anticoagulant-positive plasmas (LA 1; LA 2) and a simulated lupus anticoagulant (NPP+annexin) in diagnostic clotting tests, APTT, PT and RVVT. The normal range of these tests with the reagents used is furthermore indicated.

TABLE 2

| Plasma sample | APTT [sec] | PT [sec] | RVVT [sec] |
|---|---|---|---|
| NPP | 38.0 | 13.0 | 38.8 |
| FVIII-MP | 124.3 | 14.5 | 44.5 |
| anti-FVIII-P | 133.6 | 13.5 | 38.0 |
| LA 1 | 56.5 | 14.5 | 136.3 |
| LA 2 | 55.4 | 14.5 | 133.3 |
| NPP + 63 mg/l annexin | 81.7 | 15.0 | 122.6 |
| normal range | 26–38 sec | 10–13 sec | 31–45 sec |

EXAMPLE 2

Phospholipid dependence of the behavior of an annexin-containing plasma in diagnostic clotting tests in comparison with various normal and pathological plasmas.

For the testing of the phospholipid dependence, the APTT, PT and RVVT of the pathological plasmas mentioned in Example 1, and of the normal plasma pool and of a simulated lupus anticoagulant control, consisting of normal plasma pool and 125 or 63 mg/ml of annexin V, was determined using reagents which, compared with Example 1, have another phospholipid content. For the APPT, this was the reagent Pathromtin SL with a phospholipid concentration of Pathromtin SL reduced by 90% compared with Example 1. For the PT determination, Thromborel S 1:50 was diluted with 12.5 mM calcium chloride solution according to Brauer et al. (J Clin Chem Clin Biochem 1990; 28: 701). In contrast to this, for the RVVT, a lupus-sensitive reagent, i.e. with few phospholipids, is already used in the routine. For the negative control, in this example with LA confirm, a reagent having a higher phospholipid concentration was therefore employed. The results are shown in Table 3.

TABLE 3

Behavior of a normal plasma pool (NPP), a plasma with factor deficiency (FVIII-MP) or inhibitor against Factor VIII (anti-FVIII-P), natural lupus anti-coagulant-positive plasmas (LA 1; LA 2) and a simulated lupus anticoagulant (NPP+annexin) in diagnostic clotting tests, APTT, PT and RVVT, with altered phospholipid content (PL) compared with Example 1.

| Plasma sample | APTT [sec] PL reduced | PT [sec] PL reduced | RVVT [sec] PL increased |
|---|---|---|---|
| MPP | 45.5 | 21.5 | 34.0 |
| FVIII-MP | 130.6 | 27.6 | 37.0 |
| Anti-FVIII-P | 178.2 | 24.2 | 35.8 |
| LA 1 | 162.7 | 44.8 | 45.5 |
| LA 2 | 156.8 | 39.7 | 42.0 |
| NPP + 63 mg/l annexin | 211.6 | 54.0 | 34.7 |
| normal range | 32–49 sec | 16–27 sec | 34–51 sec |

Since in the presence of many phospholipids disturbance of the clotting by lupus anticoagulant is lowered, the quotient of the clotting time in the presence of few phospholipids to that in the presence of many phospholipids was formed from the clotting times obtained in Tables 2 (Example 1) and 3 (see Table 4). A shortening of the clotting time on account of the neutralization of the inhibitory action of a lupus anticoagulant is expressed in an increased quotient. The permissible highest limits determined for these reagents, below which a lupus anticoagulant is not suspected, are shown in Table 4 for the reagents used here.

It can be seen that the normal plasma pool, even in the presence of a factor deficiency, produces quotients in the normal range in all tests. The plasma with a specific inhibitor, on the other hand, is only still pathological in the APTT ratio. For the natural lupus anticoagulant-containing plasmas, as well as for the simulated lupus anticoagulant plasma according to the invention, a nonspecific reaction with phospholipids was otained in all 3 tests as a result of quotients which were clearly increased compared with the normal range.

TABLE 4

Calculation of the phospholipid dependence of a normal plasma pool (NPP), a plasma with factor deficiency (FVIII-MP) or inhibitor against Factor VIII (anti-FVIII-P), natural lupus anticoagulant-positive plasmas (LA 1; LA 2) and a simulated lupus anticoagulant (NPP+annexin) in diagnostic clotting tests, APTT, PT and RVVT, by formation of the quotient of the clotting time in the presence of few phospholipds to that in the case of many phospholipids. The permissible threshold value of the quotient, above which a lupus anticoagulant is suspected, is furthermore indicated.

| Plasma sample | APTT ratio | PT ratio | RVVT ratio |
|---|---|---|---|
| NPP | 1.2 | 1.7 | 1.1 |
| FVIII-MP | 1.1 | 1.9 | 1.2 |
| anti-FVIII-P | 1.3 | 1.8 | 1.1 |
| LA 1 | 2.9 | 3.1 | 3.0 |
| LA 2 | 2.8 | 2.7 | 3.2 |
| NPP + 63 mg/l annexin | 2.6 | 3.6 | 3.5 |
| upper limiting value | 1.2 | 2.1 | 1.3 |

EXAMPLE 3

Behavior of an annexin-containing plasma and various pathological plasmas in the plasma exchange experiment.

The plasma exchange experiment -was carried out in the APTT using Pathromtin SL. For this purpose, the pathological plasmas mentioned in Example 1 as well as the simulated lupus anticoagulant-positive plasma 3+1, 1+1 and 1+3 were mixed with a normal plasma pool and the APTT was determined. The results are shown in Table 5.

TABLE 5

Behavior of a plasma with factor deficiency (FVIII-MP) or inhibitor against Factor VIII (anti-FVIII-P), natural lupus anticoagulant-positive plasmas (LA 1; LA 2) and a simulated lupus anticoagulant (NPP+annexin) in the plasma exchange experiment. The APTT is indicated (by means of Pathromtin SL) in sec in various mixtures (3+1, 1+1, 1+3; sample+NPP) with a normal plasma pool (NPP).

| Plasma sample | 3 + 1 | 1 + 1 | 1 + 3 |
|---|---|---|---|
| FVIII-MP | 56.9 | 48.9 | 46.5 |
| anti-FVIII-P | 125.4 | 88.5 | 64.8 |
| LA 1 | 142.3 | 123.7 | 105.5 |
| LA 2 | 137.7 | 118.0 | 101.6 |
| NPP + 63 mg/l annexin | 184.3 | 171.2 | 139.6 |
| NPP + 7.5 mg/l annexin | 81.6 | 63.5 | 56.6 |

In the case of a mixture of 1 part of normal plasma pool with 3 parts of the plasmas ("3+1" in Table 5), all pathological plasmas as well as the simulated lupus anticoagulant-positive plasma react pathologically. In the case of a 1+1 dilution, the deficiency in the factor-deficient plasma is already completely compensated (upper limit of the normal range 50 sec).

The two natural lupus anticoagulant-positive plasmas, the annexin-containing plasmas, as well as the factor inhibitor-containing plasma are still highly pathological in the test even at higher dilution (1+3).

What is claimed is:

1. A control and/or calibration plasma for use in clotting tests comprising at least 62.5 mg/l of annexin or a mixture of annexins added to a suitable matrix to simulate a lupus anticoagulant, wherein the control and/or calibration plasma prolongs clotting time in the activated partial thromboplastin time (APTT) clotting test by at least 115% greater than the upper standard range.

2. A control and/or calibration plasma as claimed in claim 1, wherein the matrix is a natural plasma and wherein one annexin or a mixture of annexins is added in a concentration such that
   the clotting time in at least two different clotting tests is prolonged beyond the normal range, and
   said prolonged clotting time is dependent on the phospholipid content in a test batch, and
   when used as a control in a plasma exchange experiment with a normal, human plasma, the clotting time is above a normal range.

3. A control and/or calibration plasma as claimed in either of claims 1 or 2, wherein the annexin or mixture of annexins is isolated from natural sources or is of recombinant origin.

4. A control and/or calibration plasma as claimed in claim 1, wherein the matrix is a plasma of human and/or nonhuman origin.

5. The control and/or calibration plasma as claimed in claim 4, wherein the matrix is a plasma of human origin.

6. The control and/or calibration plasma as claimed in claim 4, wherein the matrix is a plasma from normal animals or normal donors.

7. The control and/or calibration plasma as claimed in claim 4, wherein the matrix is a plasma having a deficiency of a humoral system factor, which deficiency is either of a natural origin or produced artificially.

8. The control and/or calibration plasma as claimed in claim 7, wherein the deficiency is produced artificially by affinity or immunochromatography.

9. The control and/or calibration plasma as claimed in claim 4 wherein, for stabilization or for the avoidance of undesired side reactions, additives selected from the group consisting of sugars, amino acids, alcohols, natural and synthetic inhibitors of proteases, and chelating agents, antioxidants, antibiotics and azides, are added.

10. A clotting test for the determination of lupus anticoagulant comprising measuring clotting time or activity of a sample and measuring clotting time or activity of the control and/or calibration plasma as claimed in claim 1.

11. A clotting test as claimed in claim 10, which comprises selecting the concentration of annexin or mixture of annexins such that when performing the clotting test, at different phospholipid concentrations, a quotient of clotting time activity is obtained which lies outside the quotient obtained with normal, human plasma without the addition of annexin or a mixture of annexins in the same test.

12. A clotting test as claimed in claim 10, which comprises selecting the concentration of annexin or mixture of annexins such that when the annexin-containing plasma is used as a control in a plasma exchange experiment with a normal plasma, a pathological result is obtained when the mixing ratio of control to normal plasma is from 1:1 to 1:3.

13. The clotting test as claimed in claim 12, wherein a pathological result is obtained when the mixing ratio of control to normal plasma is 1:3.

14. A clotting test for the determination of lupus anticoagulant as claimed in claim 10, which comprises a diagnostic test selected from the group consisting of the activated partial thromboplastin time (APTT), the partial thromboplastin time (PT), the Russell's viper venom time (RWVT), and the kaolin clotting time (KCT).

15. A clotting test for the determination of lupus anticoagulant as claimed in claim 10, which comprises a clotting test in which a phospholipid-dependent reaction of individual, activated clotting factors takes place.

16. A clotting test according to claim 15, wherein the individual clotting factors include Factor VIIa, Factor IXa, Factor Xa, thrombin, and protein Ca.

17. A clotting test for the determination of lupus anticoagulant as claimed in claim 10, which comprises detection of clotting activity by mechanical, electrical or optical detection of clot formation or detection of activation of certain proteases of clotting by addition of suitable chromogenic substrates.

18. A method of determining whether prolongation of clotting time of the control and/or calibration plasma as claimed in claim 2 in one or more clotting tests is phospholipid-dependent, comprising adding phospholipids to a test batch by a reagent, by addition to a sample, or by separate addition, with or without preincubation, to a sample of the control and/or calibration plasma and measuring clotting time.

19. The method as claimed in claim 18, wherein the phospholipids are synthetic or natural phospholipids, are in uni- or multilamellar form, and are in undefined or in defined organization.

20. The method as claimed in claim 19, wherein the phospholipids are derived from placenta, platelets and plant extracts.

21. The method as claimed in claim 19, wherein the phospholipids are in hexagonal arrangement.

22. The method as claimed in claim 19, wherein the phospholipid content of the reagent is reduced by dilution with suitable solvents.

* * * * *

UNITED STATES PATENT AND TRADEMARK OFFICE
CERTIFICATE OF CORRECTION

PATENT NO. : 6,194,214 B1
DATED : February 27, 2001
INVENTOR(S) : Michael Kraus

It is certified that error appears in the above-identified patent and that said Letters Patent is hereby corrected as shown below:

Column 8, claim 11,
Line 59, after "clotting time", insert -- or --.

Column 9, claim 14,
Line 8, "(RWVT)" should read -- (RVVT) --.

Column 10, claim 18,
Line 5, "to a sample" should read -- of a sample --.
Line 7, "plasma" shoud read -- standard --.

Signed and Sealed this

Nineteenth Day of February, 2002

Attest:

Attesting Officer

JAMES E. ROGAN
*Director of the United States Patent and Trademark Office*